United States Patent
Butts

(10) Patent No.: US 9,028,682 B2
(45) Date of Patent: May 12, 2015

(54) SYSTEM AND METHOD FOR H2S REMOVAL INTEGRATED WITH STINSON PROCESS CO2 REMOVAL

(71) Applicant: Butts Properties, LTD., Midland, TX (US)

(72) Inventor: Rayburn C. Butts, Midland, TX (US)

(73) Assignee: Butts Properties, Ltd., Midland, TX (US)

( * ) Notice: Subject to any disclaimer, the term of this patent is extended or adjusted under 35 U.S.C. 154(b) by 0 days.

(21) Appl. No.: 13/834,276

(22) Filed: Mar. 15, 2013

(65) Prior Publication Data
US 2014/0275691 A1    Sep. 18, 2014

(51) Int. Cl.
| | | |
|---|---|---|
| F01M 11/00 | (2006.01) | |
| C07C 7/11 | (2006.01) | |
| B01D 53/14 | (2006.01) | |
| C07C 7/04 | (2006.01) | |

(52) U.S. Cl.
CPC .............. *C07C 7/11* (2013.01); *B01D 53/1425* (2013.01); *C07C 7/04* (2013.01)

(58) Field of Classification Search
None
See application file for complete search history.

(56) References Cited

U.S. PATENT DOCUMENTS 7,883,569 B2    2/2011    Stinson

OTHER PUBLICATIONS

UOP Selexol Technology for Acid Gas Removal, 2009; downloaded from http://www.uop.com/?document=uop-selexol-technology-for-acid-gas-removal&download=1.
Dow article, New Hybrid Solvent Application at the Westcoast Gas Services, Inc. Jedney Gas Plant, Sterner, et al. 1998; downloaded from http://www.dow.com/gastreating/solution/ngp_hs.htm.

*Primary Examiner* — Tam M Nguyen
(74) *Attorney, Agent, or Firm* — Ross Barnes LLP; Monty L. Ross; Robin L. Barnes

(57) ABSTRACT

A system and method for efficiently removing hydrogen sulfide from a natural gas feed stream to produce a Stinson Process feed stream and an acid gas stream. A first solvent separates the majority of the carbon dioxide and hydrocarbons from the hydrogen sulfide in the natural gas feed to produce the Stinson feed stream. By removing the majority of the hydrogen sulfide prior to feeding the Stinson Process, a carbon dioxide stream suitable for use in flooding operations may be produced with the Stinson Process. The system and method also increase the concentration of hydrogen sulfide in the acid gas stream, making it suitable for sulfur recovery operations. The system and method are particularly suitable for natural gas feed streams containing 0.5%-20% hydrogen sulfide and at least 20% carbon dioxide. Operation in an anhydrous mode with the addition of nitrogen aids in solvent recovery for recycling.

1 Claim, 2 Drawing Sheets

SYSTEM AND METHOD FOR H2S REMOVAL INTEGRATED WITH STINSON PROCESS CO2 REMOVAL

BACKGROUND OF THE INVENTION

1. Field of the Invention

This invention relates to a system and method for removing hydrogen sulfide from carbon dioxide, methane and other components of natural gas streams being processed into a sales gas stream. The system and method of the invention are particularly suitable to separate carbon dioxide and hydrogen sulfide when the Stinson Process is utilized for removing high concentrations of carbon dioxide and hydrogen sulfide from natural gas streams containing nitrogen.

2. Description of Related Art

Hydrogen sulfide and carbon dioxide contamination are frequently encountered problems in the production of natural gas. Transporting pipelines typically do not accept natural gas containing more than about 4% $CO_2$ and 4 ppm hydrogen sulfide. Hydrogen sulfide is particularly problematic because it is extremely toxic to humans and is corrosive in nature. Allowing hydrogen sulfide to remain in process streams can be harmful to piping and other equipment. As such, it is desirable to remove $H_2S$ from the produced gas early in the processing.

Known methods of removing $H_2S$ and $CO_2$ from natural gas streams include chemical solvents and physical solvents. These technologies have been well tested in the natural gas industry and the strengths and weaknesses of various chemical components used in these processes are well known to those in the industry. One such physical solvent that is well established in the industry is Selexol from Dow Chemical. With a typical Selexol process, the feed gas contacts the Selexol in a first absorber, where the majority of the $CO_2$ and $H_2S$ in the feed stream are removed into the solvent. The $CO_2$ and $H_2S$ are then separated through one or more reduced pressure separators and a stripper to produce a $CO_2$ and $H_2S$ rich "acid gas" vapor stream and a "Lean" Selexol stream to be recycled back to the inlet absorber where it removes more $CO_2$ and $H_2S$ from incoming gas. Utilization of conventional Selexol technology is used where the $CO_2$ concentrations are generally in the 10 to 20 percent range and are used in preference to chemical processes based on the comparative installation cost and the cost of operation.

Another known method for removing both $CO_2$ and $H_2S$ from natural gas is known as the Stinson Process, as described in U.S. Pat. No. 7,883,569 and the patents related thereto. The Stinson Process takes a dehydrated feed stream containing around 70% $CO_2$, 20% $CH_4$, 7% $N_2$, and 3.5% $H_2S$ and produces a processed gas stream containing around 3% $N_2$, 97% $CH_4$, and 0.03% $H_2S$ and a liquid waste stream containing around 94% $CO_2$ and 5% $H_2S$. The $CO_2$ and $H_2S$ are removed from the feed stream using a fractionating column, with the bottom stream containing primarily $CO_2$ and some $H_2S$ and an overhead stream containing 31% $CO_2$ and less than 2% $H_2S$. The overhead stream from the fractionating column is then processed using a methanol absorption tower to separate additional $CO_2$ and $H_2S$ and produce an intermediate processed gas stream (containing around 69% methane) as the overhead stream from the absorption tower, which is then processed through a separator to remove nitrogen and helium, resulting in a processed gas stream containing around 97% $CH_4$ and around 0.03% $H_2S$. This processed gas stream is then typically passed through a molecular sieve to scrub the 300 ppm $H_2S$ down to an acceptable pipeline level of less than 4 ppm for sales gas. The methanol is then recovered using a flash chamber and a methanol stripper tower, with the recovered methanol being recycled back to the methanol absorption tower. The overhead streams from the flash chamber and methanol stripper contain $CO_2$, $CH_4$, and $H_2S$ and are recycled back to feed the fractionating column. The liquid waste stream from the fractionating column, which contains around 94% $CO_2$ and 5% $H_2S$ may be injected into an underground well, avoiding some of the environmental concerns associated with releasing $CO_2$ and $H_2S$ to the atmosphere.

SUMMARY OF THE INVENTION

The system and method disclosed herein facilitate the economically efficient and selective removal of $H_2S$ from a feed gas stream containing methane and $CO_2$ using a solvent. The system and method of the invention are particularly suitable for integrated use in connection with the Stinson Process for removing $CO_2$, wherein the solvent used to remove the $H_2S$ is different from the solvent used to remove $CO_2$ and the majority of the $H_2S$ is removed upstream from the $CO_2$ removal. Natural gas processing using the prior art Stinson Process, with around 3.5% $H_2S$ in the feed stream, generally results in a sales gas (hydrocarbon) stream containing no $CO_2$ (or less than 4 ppm $CO_2$) and around 4 ppm of $H_2S$, and a $CO_2$ waste stream containing around 47,000 ppm $H_2S$. The methanol stripping in the Stinson Process will reduce the level of $H_2S$ from 3.5% in the feed to around 0.03% (300 ppm), which is further reduced to 4 ppm or less after passing through a molecular sieve to produce an acceptable sales gas. While the amount of $H_2S$ in the sales gas stream may be within pipeline specifications, the amount in the waste stream limits the ability to use the $CO_2$ waste stream for flooding operations. Typically, the $H_2S$ specification for $CO_2$ flood streams is less than 100 ppm. Removing the majority of the $H_2S$ upstream of the Stinson Process according to the invention increases the overall process efficiencies, including a reduction in operating costs through fuel savings, while allowing production of a processed $CO_2$ stream from the Stinson Process that is well within specifications for allowing use of that stream in flooding operations. The processed $CO_2$ stream can also be delivered to the pipeline as a liquid stream, which has significant cost savings over injecting as a vapor. By reducing the $H_2S$ level in the Stinson Process feed to a preferable level less than 50 ppm, it may be unnecessary to use a molecular sieve after the Stinson Process to achieve a sales gas stream with an acceptable $H_2S$ level, which may offset some of the capital costs associated with the invention and saves on operating costs. Additionally, the use of two different solvents, a first solvent to remove $H_2S$ and a second solvent to remove $CO_2$, where the solubility of $H_2S$ relative to $CO_2$ in the first solvent is greater than the relative solubility in the second solvent, further increases the efficiencies of the overall process.

Through the use of the invention, the 3.5% (35,000 ppm) $H_2S$ typically found in the Stinson Process feed stream is substantially reduced. According to the invention, the processed gas stream that feeds the Stinson Process fractionating column preferably contains less than 50 ppm (0.005%) of $H_2S$, but may contain up to 150 ppm or more $H_2S$ depending on the amount of $H_2S$ in the gas stream feeding the system of the invention, although the amount of $H_2S$ is still significantly less than the 35,000 ppm in a typical Stinson feed stream. Consequently, only trace amounts of $H_2S$ are present in the final sales gas (hydrocarbon) stream and in the processed $CO_2$ stream using the $H_2S$ removal methods according to the invention integrated with the Stinson Process. Additionally, the concentrated $CO_2$ waste stream in the typical Stinson Process has around 94% $CO_2$ and 5% $H_2S$, which is too much $H_2S$ to allow use of the $CO_2$ in flooding operations, but not enough $H_2S$ to allow for recovery of sulfur—making it truly a waste stream. By first reducing the $H_2S$ level in the Stinson feed according to the invention, the processed $CO_2$ stream produced from the Stinson Process fractionating column has sufficiently low levels of $H_2S$ to permit use in flooding operations. Additionally, the acid gas stream of the present invention contains 0.5%-50% (or more) $H_2S$, but preferably contains at least 30% $H_2S$. The amount of $H_2S$ in the acid gas stream will depend on the amount of $H_2S$ in the stream that feeds the system of the invention. The preferred higher concentration levels for $H_2S$ in the acid gas stream of the present invention make that stream suitable for feeding a Claus Process to recover sulfur from the $H_2S$, if desired. Thus the use of the invention integrated with the Stinson Process allows reuse of what would otherwise be waste streams with prior art processes. Alternatively, the volume of the acid gas stream according to the invention is relatively smaller than a traditional Stinson Process acid gas ($CO_2$ waste) stream, making it easier to dispose of the $H_2S$ if further processing is not desired.

According to one embodiment of the invention, a system and method are disclosed for strategically integrating an $H_2S$ removal system into a typical Stinson Process operation. The feed stream that normally feeds the fractionating column (after passing through dehydration beds and a heat exchanger) in the Stinson Process is first processed through the $H_2S$ removal system of the present invention. After preferably being dehydrated, the feed stream passes through an absorber, where $H_2S$ is selectively absorbed by the use of DEPG (dimethyl ether polyethylene glycol, available from Dow Chemical under the trademark SELEXOL®) or a similar solvent. Most preferably, the removal operation is anhydrous. The vapor stream exiting the absorber is the Stinson Process feed stream that preferably feeds directly to the fractionating column in the Stinson Process and then being processed as disclosed in U.S. Pat. No. 7,883,569, which is incorporated herein by reference. The liquid stream exiting the absorber then feeds a series of separators and a stripper to recover the DEPG solvent and produce an acid gas stream preferably containing around 50% $CO_2$ and around 30-40% $H_2S$.

According to another embodiment of the invention, nitrogen is fed to the stripper to enhance separation of the DEPG from the $CO_2$ and $H_2S$. Preferably, the nitrogen is supplied from an onsite Nitech™ NRU (such as that described in U.S. Pat. No. 5,141,544), to provide enhanced efficiencies; but other sources of nitrogen may be used. Typically, water or steam is used to regenerate the DEPG. The addition of nitrogen to the stripper enhances the recovery of the DEPG when operating in an anhydrous mode, according to a preferred embodiment of the invention. Additionally, an anhydrous operation results in further cost savings, since lower cost metals may be used in equipment fabrication.

There are several advantages to the system and method disclosed herein not previously achievable by those of ordinary skill in the art using existing technologies. These advantages include, for example, the system and method allow for the $CO_2$ stream produced through the Stinson Process to be within pipeline specifications for use in flooding operations, rather than be treated as a waste stream requiring disposal. The system and method also allow for removal of the corrosive $H_2S$ prior to processing in the Stinson Process and results in an acid gas stream having sufficiently high concentration of $H_2S$ to allow further processing for recovery of sulfur, if desired. By integration with common utilities utilized by the Stinson Process, the cost of new equipment is reduced. Because the $H_2S$ is highly soluble in the methanol used in the Stinson Process, the removal of the $H_2S$ prior to the Stinson Process will enhance the removal of $CO_2$ in the Stinson Process. Additionally, the system and method of the invention require low regeneration of heat, using only 30%-50% of the energy required for conventional technologies to separate out $H_2S$. The system and method of the invention are particularly well suited for feed streams containing 20% or more $CO_2$.

Although the present system and method has the disadvantage of higher capital costs associated with additional equipment for the $H_2S$ removal, the costs of such are sufficiently offset by the savings in having a usable Stinson Process $CO_2$ stream and savings in operating costs achieved by strategically placing the $H_2S$ removal upstream of the Stinson Process to take advantage of inter-operational efficiencies.

Those of ordinary skill in the art will appreciate upon reading this disclosure that references to separation of $H_2S$, $CO_2$, and methane used herein refer to processing natural gas feed streams containing additional components to produce various multi-component product streams containing large amounts of the particular desired component, but not necessarily pure streams of any particular component. Additionally, those of ordinary skill in the art will understand that streams that are described herein as liquid or vapor streams are not necessarily purely in a liquid or gaseous state, but may be primarily present as a liquid or gas. Those of ordinary skill in the art will also appreciate upon reading this disclosure that additional processing sections for removing various components or contaminants that are present in the feed stream or intermediate streams, can also be included in the system and method of the invention, depending upon factors such as, for example, the origin and intended disposition of the product streams and the amounts of such other gases, impurities or contaminants as are present in the streams.

BRIEF DESCRIPTION OF THE DRAWINGS

The system and method of the invention are further described and explained in relation to the following drawings wherein.

DESCRIPTION OF PREFERRED EMBODIMENTS

Figure 1:
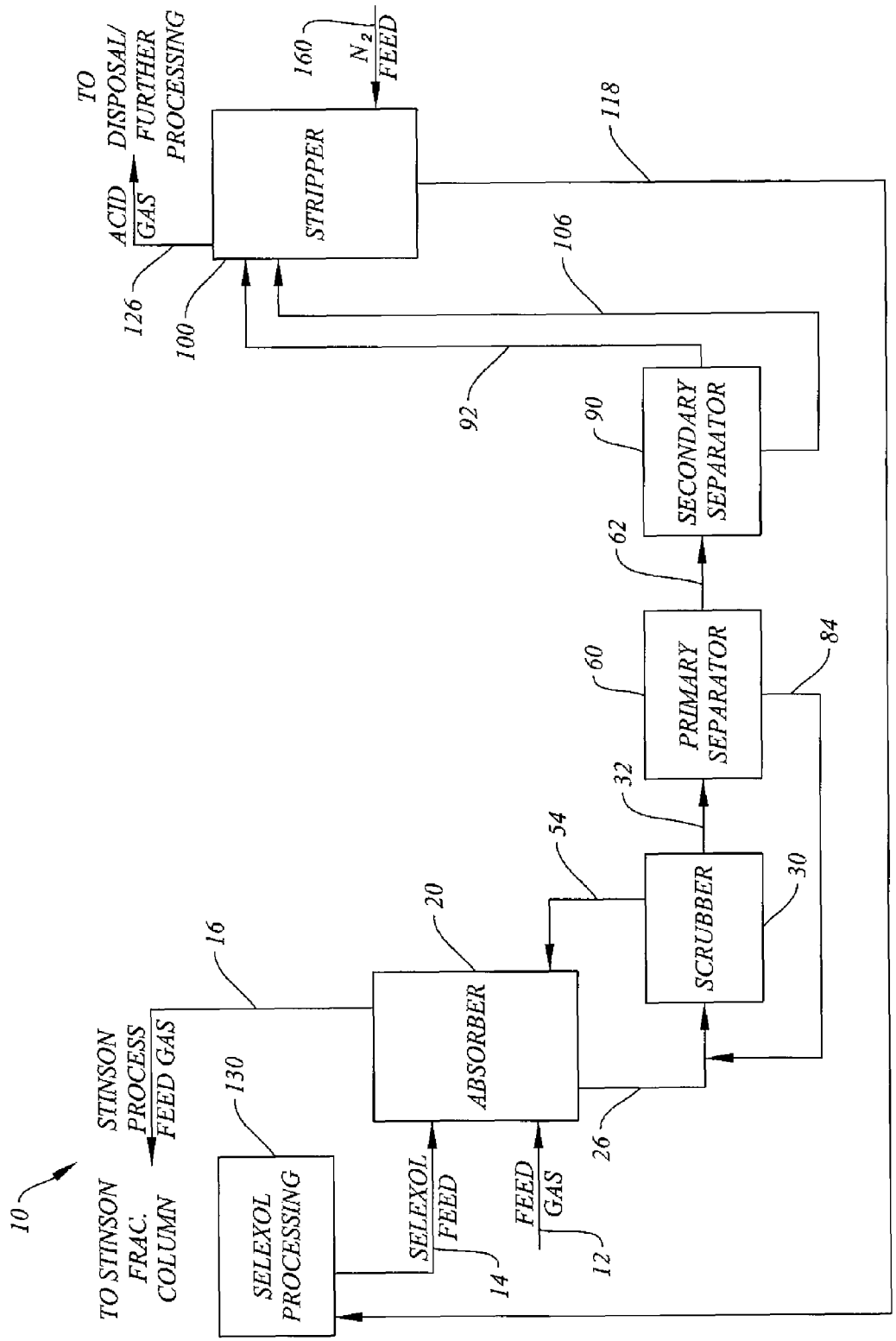
FIG. 1 is a simplified process flow diagram illustrating principal processing stages of an embodiment of a system and method for removing $H_2S$.

FIG. 1 depicts the basic processing stages of the system and method according to a preferred embodiment of the invention. The system 10 comprises processing equipment that is inserted into typical natural gas processing operations upstream of the fractionating column used in the Stinson Process. System 10 of the invention includes an absorber 20, a scrubber 30, a primary separator 60, a secondary separator 90, and a stripper 100. System 10 also includes a DPEG processing block 130, which includes pumps and heat exchangers as more fully described in relation to FIG. 2. A gas feed stream, comprising methane, hydrogen sulfide, and carbon dioxide is preferably dehydrated using known methods, such as a standard molecular sieve style water removal process, prior to entering system 10 as feed stream 12. Feed stream 12 contains methane, at least 20% $CO_2$, and at least 0.5% $H_2S$. Preferably, feed stream 12 contains 15%-25% methane, at least 50% $CO_2$, and most preferably 60%-80%

$CO_2$, 0.5%-20% $H_2S$, and most preferably 3%-6% $H_2S$, and 5%-15% nitrogen, although other feed stream compositions may be used with the invention. Feed stream 12 is fed into absorber 20. A DPEG feed stream 14 is also fed to absorber 20 to facilitate removal of $H_2S$ from the gas feed stream 12. Overhead stream 16, preferably comprising around 50 ppm $H_2S$ or less exits absorber 20 and is the feed stream to the fractionating column of the Stinson Process. Because feed stream 12 was preferably dehydrated prior to feeding absorber 20, it is not necessary to dehydrate overhead stream 16 prior to feeding the Stinson Process. It may be desirable to pass overhead stream 16 through a heat exchanger prior to feeding the fractionating column of the Stinson Process or stream 16 may be fed directly to the fractionating column.

Bottom stream 26 is combined with a first carbon dioxide recycle stream 84 to feed scrubber 30. Carbon dioxide recycle stream 84 comprises primarily $CO_2$, with some $H_2S$ and small amounts of other compounds. Vapor stream 54 is recycled from the scrubber 30 back to a bottom level of the absorber 20. Liquid stream 32 exits scrubber 30 and feeds primary separator 60. Carbon dioxide recycle vapor stream 84 and liquid stream 62 exit primary separator 60. Liquid stream 62 feeds secondary separator 90. Vapor stream 92 and liquid stream 106 exit secondary separator 90 to feed stripper 100. A nitrogen feed stream 160 may also be fed to a bottom level of stripper 100, if desired. Stripper 100 purifies the DPEG from the feed streams to recycle it back to the DPEG processing block 130 via stream 118. Acid gas stream 126, preferably containing 35%-55% carbon dioxide, 5%-15% nitrogen, and 30%-50% hydrogen sulfide, exits stripper 100 as the overhead stream and may either be disposed of or may be feed to a Claus process to recover sulfur, if desired.

Figure 2:
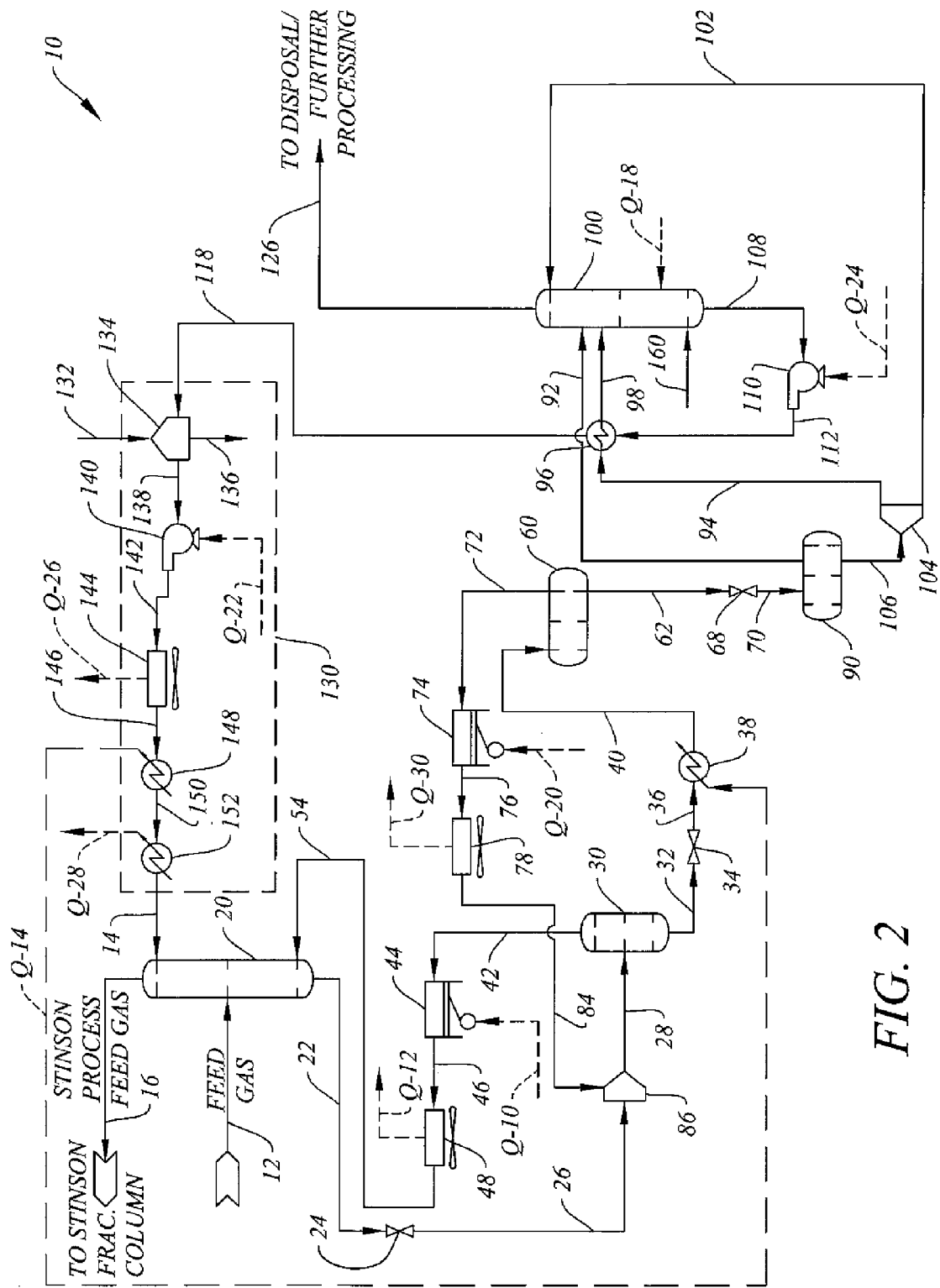
FIG. 2 is a more detailed process flow diagram illustrating the processing stages of a preferred embodiment of a system and method for removing $H_2S$.

A preferred embodiment of system 10 is depicted in greater detail in FIG. 2. Referring to FIG. 2, a 200 MMSCFD feed stream 12 containing approximately 19.5% methane, 7% nitrogen, 3.7% $H_2S$, and 69.1% $CO_2$ at 79.9° F. and 671.9 psia feeds a middle stage of absorber 20. The water content in stream 12 is extremely low, and most preferably zero, as it has first been dehydrated by means of a molecular sieve unit according to a preferred embodiment of the invention. Absorber 20 is also fed at an upper stage by a first solvent feed stream 14 and at a lower stage by a recycle stream 54. A Stinson Process feed stream 16 exits as the overhead stream from absorber 20. Bottoms stream 22 exits the bottom of absorber.

Stinson Process feed stream 16 comprises approximately 21.5% methane, 7.7% nitrogen, 0.002% $H_2S$, and 70% $CO_2$ at 95.4° F. and 670.1 psia. Stinson Process feed stream 16 preferably contains between 60%-70% of the total amount of $CO_2$ fed into absorber 20 and at least 80% of the $CO_2$ in feed stream 12. After exiting absorber 20, Stinson Process feed stream 16 is then preferably fed to the Stinson Process. As disclosed in U.S. Pat. No. 7,833,569, the Stinson Process feed stream (stream 16 according to the present invention), passes through a heat exchanger before entering a fractionating column. Typically, the Stinson Process feed stream is also dehydrated prior to entering the fractionating column. Because the feed stream 12 is dehydrated prior to entering absorber 20 according to a preferred embodiment of the invention, it is not necessary to dehydrate Stinson Process feed stream 16 prior to feeding the Stinson Process fractionating column. The vapor stream from the fractionating column and a second solvent feed stream (preferably methanol) feed an absorption tower, with a processed gas stream exiting as the vapor stream from the absorption tower. This vapor stream then becomes the final sales gas stream after passing through a molecular sieve in a typical Stinson Process, although it is not necessary to use a molecular sieve to achieve acceptable levels of $H_2S$ in the sales gas stream when the Stinson feed stream is processed according to the invention. The liquid stream from the absorption tower then feeds a flash chamber, with the liquid stream from the flash chamber feeding a methanol stripper. The vapor streams from the flash chamber and stripper are carbon dioxide recycle streams, comprising primarily carbon dioxide and some methane and hydrogen sulfide along with trace amounts of other compounds that feed back into the fractionating column. The liquid stream from the stripper is a solvent recycle stream that feeds back into the solvent feed stream. The liquid stream from the fractionating column in the typical Stinson Process is a $CO_2$ waste stream that is injected into an underground well. However, the high $CO_2$ and low $H_2S$ concentrations in feed stream 16 according to the invention result in the processed $CO_2$ stream in the Stinson Process (stream no. 60 in the Stinson '569 patent) having an $H_2S$ concentration well within pipeline specification for use in $CO_2$ flooding operations, so that the $CO_2$ stream may be reused and does not require immediate disposal. Most preferably, the Stinson Process fractionating column bottoms stream comprises at least 90% $CO_2$ and less than 4 ppm $H_2S$ when the fractionating column is fed with stream 16 according to the invention. The Stinson Process system, and preferred parameters for operation, are more fully described in the '569 patent.

Referring again to FIG. 2, DEPG (such as Selexol®) is a preferred solvent for use in solvent feed stream 14 according to the invention because of its higher affinity for $H_2S$ over $CO_2$. The solubility of $H_2S$ in DEPG is around nine times greater than that of $CO_2$, allowing the bulk of the $CO_2$ in feed stream 12 to pass through absorber 20 and exit as Stinson Process feed stream 16. Preferably, stream 16 contains more than 80% of the $CO_2$ present in feed stream 12 and more than 60% of the total $CO_2$ fed to absorber 20 by feed stream 12 and recycle stream 54. Although DEPG is a preferred solvent, other solvents may be used within the scope of the invention. Additionally, the preferred solvent for use in the Stinson Process is methanol, but other solvents may be used with that process according to the invention. Most preferably, the first solvent used in absorber 20 is different from the second solvent used in the Stinson Process, with the solubility of $H_2S$ relative to $CO_2$ in the second solvent being less than the relative solubility in the first solvent. System 10 is also preferably operated in an anhydrous mode, with no water being added to the first solvent feed or added to stripper 100 (discussed below).

Bottom stream 22 exits the bottom of absorber 20, containing approximately 0.007% methane, negligible nitrogen, 36.6% DEPG, 7.9% $H_2S$, and 55.4% $CO_2$ at 110.1° F. and 672.1 psia. Bottom stream 22 passes through liquid level control valve 24, exiting the valve as stream 26 at 86° F. and 310 psia. The liquid entering valve 24 is capable of cooling by the well-known Joule-Thomson effect. Stream 26 is mixed with stream 84 in mixer 86, exiting as combined stream 28 containing approximately 29.95% DEPG, 7.8% $H_2S$, and 62.1% $CO_2$. Combined stream 28 feeds scrubber 30, where the majority of the $CO_2$ is separated for recycling back to absorber 20. Overhead vapor stream 42 and bottom liquid stream 32 exit scrubber 30 containing approximately 60.5% and 39.5%, respectively, of the $CO_2$ fed to scrubber 30. Overhead stream 42 also contains approximately 4% $H_2S$ and a negligible amount of DEPG, while bottom stream 32 contains approximately 10.3% $H_2S$ and 49.3% DEPG. Overhead stream 42 is compressed by compressor 44, exiting as stream 46 at 236.9° F. and 700 psia. Compressor 44 receives energy, designated as energy stream Q-10. Stream 46 then passes through heat exchanger 48, exiting as stream 54 cooled to at 110° F. Heat exchanger 48 releases heat, designated by energy stream Q-12. Stream 54, a carbon dioxide recycle stream, is fed into a bottom stage of absorber 20. Stream 54 contains approximately 95.9% $CO_2$ and 4% $H_2S$ at 695 psia.

Bottom stream 32 exits scrubber 30 and passes through liquid level valve 34, exiting as stream 36 having the pressure reduced from 305 psia to 120 psia and a drop in temperature of approximately 20° F. Stream 36 passes through heat exchanger 38, which receives energy (designated as energy stream Q-14) released from heat exchanger 148, and exits as stream 40 having been warmed from 66.5° F. to 93.4° F. Stream 40 feeds primary flash gas separator 60, with vapor stream 72 and liquid stream 62 exiting the separator 60. Vapor stream 72, another carbon dioxide recycle stream containing approximately 92.6% $CO_2$, and 7.2% $H_2S$ at 93.4° F. and 115 psia passes through compressor 74 exiting as stream 76 at 266.6° F. and 315 psia. Compressor 74 is supplied with energy designated as energy stream Q-20. Stream 76 passes through heat exchanger 78 where it is cooled to 110° F. as stream 84. Heat exchanger 78 releases heat energy designated as energy stream Q-30. Stream 84 is then mixed with stream 26 in mixer 86 to feed scrubber 30 as combined stream 28.

Liquid stream 62, containing approximately 18.1% $CO_2$, 11.6% $H_2S$, and 70.2% DEPG at 93.4° F. and 115 psia, passes through level control valve 68, exiting the valve as partially vaporized stream 70 with a pressure drop of approximately 48 psi. Stream 70 feeds secondary flash gas separator 90, exiting as vapor stream 92 and liquid stream 106, both streams at 87.4° F. and 65 psia. Vapor stream 92, containing 89.7% $CO_2$ and 10.1% $H_2S$ feeds an upper stage of stripper 100. Liquid stream 106, containing 11.6% CO2, 11.7% H2S and 76.6% DEPG is split by splitter 104 into streams 94 and 102. Stream 102 feeds stripper 100. Stream 94 passes through heat exchanger 96, exiting as stream 98 having been heated to 288.2° F. and partially vaporized. Stream 98 feeds an intermediate stage of stripper 100. Optionally, a nitrogen feed stream 160, containing near 100% $N_2$ at 80° F. and 25 psia, may also feed a lower stage of stripper 100. The addition of nitrogen feed stream 160 to stripper may result in increased recovery of the DEPG solvent. In the simulation example described herein, stream 160 has a flow rate of 2.5 MMSCFD.

Stripper 100 strips the DEPG from the other components so that the DEPG may be recycled back to absorber 20. Bottom liquid stream 108, containing 99.9% DEPG at 297.8° F. and 17.5 psia, exits stripper 100 and is pumped by pump 110, exiting as stream 112 at 65 psia. Pump 110 receives energy designated as energy stream Q-24. Stream 112 passes through heat exchanger 96 for heat transfer with stream 94. Stream 112 exits heat exchanger 96 as stream 118 at a temperature of 105.6° F. Stream 118 enters a makeup block 134 where additional DEPG may be added or bled off via streams 132 or 136. Stream 138 exits the makeup block 134 containing approximately 99.9% DEPG, no water, and small amounts of nitrogen and hydrogen sulfide at around 105.6° F. and 60 psia. Stream 138 is pumped through pump 140, supplied by energy designated as energy stream Q-22. Stream 142 exits pump 140 with the pressure increased to 715 psia. Stream 142 passes through heat exchanger 144 and exits as stream 146 cooled to 110° F. Stream 146 then passes through second and third heat exchangers, 148 and 152, ultimately exiting as DEPG feed stream 14 having a temperature of 40° F. and a pressure of 700 psia. Stream 14 feeds an upper stage of absorber 20. Heat exchangers 144, 148, and 152 release heat energy designated as energy streams Q-26, Q-14, and Q-28, respectively.

Overhead vapor (or acid gas) stream 126 exits stripper 100 containing 53.9% $CO_2$, 34.4% $H_2S$ and 11.5% $N_2$ at a temperature of 80.7° F. and a pressure of 15.5 psia. Acid gas stream 126 may be properly disposed of or may feed other processing equipment to recover sulfur.

EXAMPLE

The flow rates, temperatures and pressures of various simulation flow streams referred to in connection with the discussion of the system and method of the invention in relation to FIG. 2 for a feed gas stream flow rate of approximately 200 MMSCFD and containing 7% nitrogen, 19.5% methane, 69.1% $CO_2$, and 3.7% $H_2S$ appear in Table 1 below. The values for the energy streams referred to in connection with the discussions of the system and method of the invention in relation to FIG. 2 appear in Table 2 below. The values discussed herein and in the tables below are approximate values.

TABLE 1

FLOW STREAM PROPERTIES

| Stream Ref. No. | % $N_2$ | % CO2 | % H2S | % $CH_4$ | % DEPG | Flow Rate (lbmol/h) | Temp. (deg. F) | Press. (psia) |
| --- | --- | --- | --- | --- | --- | --- | --- | --- |
| 12 | 7 | 69.1 | 3.7 | 19.5 | 0 | 21956 | 79.9 | 671.9 |
| 14 | 0.098 | 0 | 0.012 | 0 | 99.89 | 4889.3 | 40 | 700 |
| 16 | 7.7 | 70 | 0.002 | 21.5 | neg | 19889.1 | 95.4 | 670.1 |
| 22 | neg | 55.4 | 7.9 | 0.007 | 36.6 | 13350.3 | 110.1 | 672.1 |
| 26 | neg | 55.4 | 7.9 | 0.007 | 36.6 | 13350.3 | 86 | 310 |
| 28 | neg | 62.1 | 7.8 | 0.006 | 30 | 16306.5 | 87 | 310 |
| 32 | neg | 40.3 | 10.3 | 0.0005 | 49.3 | 9910.3 | 86.6 | 305 |
| 36 | neg | 40.3 | 10.3 | 0.0005 | 49.3 | 9910.3 | 66.5 | 120 |
| 40 | neg | 40.3 | 10.3 | 0.0005 | 49.3 | 9910.3 | 93.4 | 115 |
| 42 | neg | 95.9 | 3.98 | 0.014 | neg | 6396.2 | 86.6 | 305 |
| 46 | neg | 95.9 | 3.98 | 0.014 | neg | 6396.2 | 236.9 | 700 |
| 54 | neg | 95.9 | 3.98 | 0.014 | neg | 6396.2 | 110 | 695 |
| 62 | neg | 18.1 | 11.6 | neg | 70.2 | 6954.6 | 93.4 | 115 |
| 70 | neg | 18.1 | 11.6 | neg | 70.2 | 6954.6 | 87.7 | 67 |
| 72 | neg | 92.6 | 7.2 | 0.0017 | neg | 2955.7 | 93.4 | 115 |
| 76 | neg | 92.6 | 7.2 | 0.0017 | neg | 2955.7 | 266.6 | 315 |
| 84 | neg | 92.6 | 7.2 | 0.0017 | neg | 2955.7 | 110 | 310 |
| 92 | neg | 89.7 | 10.1 | 0.0003 | neg | 582.1 | 87.4 | 65 |
| 94 | neg | 11.6 | 11.7 | neg | 76.6 | 5735.3 | 87.4 | 65 |
| 98 | neg | 11.6 | 11.7 | neg | 76.6 | 5735.3 | 288.2 | 60 |
| 102 | neg | 11.6 | 11.7 | neg | 76.6 | 637.3 | 87.4 | 65 |

TABLE 1-continued

FLOW STREAM PROPERTIES

| Stream Ref. No. | % N$_2$ | % CO2 | % H2S | % CH$_4$ | % DEPG | Flow Rate (lbmol/h) | Temp. (deg. F) | Press. (psia) |
|---|---|---|---|---|---|---|---|---|
| 106 | neg | 11.6 | 11.7 | neg | 76.6 | 6372.5 | 87.4 | 65 |
| 108 | 0.098 | neg | 0.017 | 0 | 99.88 | 4889.6 | 297.8 | 17.5 |
| 112 | 0.098 | neg | 0.017 | 0 | 99.88 | 4889.6 | 298.2 | 65 |
| 118 | 0.098 | neg | 0.017 | 0 | 99.88 | 4889.6 | 105.6 | 60 |
| 126 | 11.5 | 53.9 | 34.4 | neg | 0.0001 | 2339.6 | 80.7 | 15.5 |
| 132 | 0 | 0 | 0 | 0 | 100 | 0 | 100 | 115 |
| 136 | 0.098 | neg | 0.017 | 0 | 99.88 | 0.029 | 105.6 | 60 |
| 138 | 0.098 | neg | 0.017 | 0 | 99.88 | 4889.5 | 105.6 | 60 |
| 142 | 0.098 | 0 | 0.012 | 0 | 99.88 | 4889.3 | 110.5 | 715 |
| 146 | 0.098 | 0 | 0.012 | 0 | 99.88 | 4889.3 | 110 | 710 |
| 150 | 0.098 | 0 | 0.012 | 0 | 99.88 | 4889.3 | 72.5 | 705 |
| 160 | 100 | 0 | 0 | 0 | 0 | 274.5 | 80 | 25 |

TABLE 2

ENERGY STREAM REPORT

| Energy Stream Reference Numeral | Energy Rate (MMBtu/h) | Power (hp) | From | To |
|---|---|---|---|---|
| Q-10 | | 3027.2 | — | Compressor 44 |
| Q-12 | 9.78 | | Heat Exchanger 48 | — |
| Q-14 | 25.34 | | Heat Exchanger 148 | Heat Exchanger 38 |
| Q-18 | 25 | 9825.4 | — | Stripper 100 |
| Q-20 | | 1768.2 | — | Compressor 74 |
| Q-22 | | 1587.3 | — | Pump 140 |
| Q-24 | | 126.5 | — | Pump 110 |
| Q-26 | 0.33 | | Heat Exchanger 144 | — |
| Q-28 | 21.1 | | Heat Exchanger 152 | — |
| Q-30 | 4.74 | | Heat Exchanger 78 | — |

Those of ordinary skill in the art will appreciate upon reading this disclosure that the values discussed above are based on the particular parameters and composition of the feed stream in the Example, and that the values can differ depending upon differences in operating conditions and upon the parameters and composition of the feed stream 12. Those of ordinary skill in the art will also appreciate upon reading the disclosure in light of the accompanying drawings that alterations and modifications of the invention may be made and it is intended that the scope of the invention disclosed herein be limited only by the broadest interpretation of the appended claims to which the inventor is legally entitled.

I claim:

1. A system for removing hydrogen sulfide from a first feed stream comprising methane, carbon dioxide, and hydrogen sulfide to produce a Stinson Process feed stream and an acid gas stream, the system comprising:

an absorber wherein the first feed stream contacts an solvent feed stream to separate the first feed stream into an absorber bottoms stream and an absorber overhead stream, the absorber bottoms stream comprising hydrogen sulfide and a substantial portion of the solvent feed stream and the absorber overhead stream comprising a substantial portion of the methane and carbon dioxide from the first feed stream;

a first separator wherein the absorber bottoms stream is separated into a first vapor stream and a first liquid stream;

a second separator wherein the first liquid stream is separated into a second vapor stream and a second liquid stream;

a third separator wherein the second liquid stream is separated into a third vapor stream and a third liquid stream;

a stripper wherein a substantial portion of the solvent feed stream is stripped from the third vapor stream and third liquid stream to produce an acid gas stream and an solvent recycle stream;

a heat exchanger for cooling the solvent recycle stream through heat exchange with the third liquid stream;

a mixer for mixing the absorber bottoms stream and the first vapor stream prior to entering the first separator; and wherein the solvent recycle stream is recycled back into the solvent feed stream, the first vapor stream is recycled back to a lower stage of the absorber, and the second vapor stream is recycled back to feed the first separator; and wherein the absorber overhead stream is the Stinson Process feed stream.

* * * * *